United States Patent
Verish et al.

(10) Patent No.: US 12,025,344 B2
(45) Date of Patent: Jul. 2, 2024

(54) COVER ASSEMBLY FOR DISINFECTING AN AIR CONDITIONER

(71) Applicant: Inceptus Incorporated, Oxford, MA (US)

(72) Inventors: Kenneth Verish, Bellingham, MA (US); Daniel Peter St.Laurent, Webster, MA (US)

(73) Assignee: VENMILL INDUSTRIES, INC., Oxford, MA (US)

( * ) Notice: Subject to any disclaimer, the term of this patent is extended or adjusted under 35 U.S.C. 154(b) by 623 days.

(21) Appl. No.: 17/144,462

(22) Filed: Jan. 8, 2021

(65) Prior Publication Data
US 2021/0222898 A1 Jul. 22, 2021

Related U.S. Application Data (60) Provisional application No. 62/962,513, filed on Jan. 17, 2020.

(51) Int. Cl.
*F24F 8/26* (2021.01)
*A61L 9/04* (2006.01)
(Continued)

(52) U.S. Cl.
CPC .............. *F24F 8/26* (2021.01); *A61L 9/046* (2013.01); *A61L 9/12* (2013.01); *F24F 13/20* (2013.01);
(Continued)

(58) Field of Classification Search
CPC .......... F24F 8/26; F24F 13/20; F24F 2221/22; A61L 9/046; A61L 9/12; A61L 2101/02;
(Continued)

(56) References Cited

U.S. PATENT DOCUMENTS

| | | | |
|---|---|---|---|
| 2011/0033346 A1* | 2/2011 | Bohlen | F24F 8/80 422/186.3 |
| 2013/0160800 A1* | 6/2013 | Steinmann | F24F 13/20 15/345 |

(Continued)

FOREIGN PATENT DOCUMENTS

| | | |
|---|---|---|
| EP | 1057923 A1 | 12/2000 |
| EP | 1745805 A1 | 1/2007 |

(Continued)

OTHER PUBLICATIONS

Halosil International, "What are 'Logs,' and Why do They Matter in Preventing Infections" Halosil Blog, https://halosil.com/what-are-logs-and-why-do-they-matter-in-preventing-infections/ (Jul. 24, 2015).

(Continued)

*Primary Examiner* — Sean E Conley
*Assistant Examiner* — Brendan A Hensel
(74) *Attorney, Agent, or Firm* — Finch & Maloney PLLC (57) ABSTRACT

A cover assembly is configured for disinfecting an air conditioning unit. The assembly includes a cover made of a pliable material that is shaped to be installed on the inside portion of an air conditioning unit. The assembly also includes an ozone generator configured to direct ozone into the air conditioning unit. A controller is operatively coupled to the ozone generator and is configured to control operation of the ozone generator.

12 Claims, 5 Drawing Sheets

FIG. 2

(51) Int. Cl.
*A61L 9/12* (2006.01)
*F24F 13/20* (2006.01)
*A61L 101/02* (2006.01)

(52) U.S. Cl.
CPC ...... *A61L 2101/02* (2020.08); *A61L 2209/111* (2013.01); *A61L 2209/15* (2013.01); *A61L 2209/16* (2013.01); *A61L 2209/212* (2013.01)

(58) Field of Classification Search
CPC ........... A61L 2209/111; A61L 2209/15; A61L 2209/16; A61L 2209/212; Y02A 50/20
See application file for complete search history.

(56) References Cited

U.S. PATENT DOCUMENTS

| | | | |
|---|---|---|---|
| 2017/0021046 A1* | 1/2017 | Drake | A61L 2/24 |
| 2019/0022262 A1* | 1/2019 | Andrews | A45C 15/00 |

FOREIGN PATENT DOCUMENTS

| | | | |
|---|---|---|---|
| EP | 1745805 | A1 | 1/2017 |
| KR | 20090071018 | A | 7/2007 |
| KR | 20090071018 | A | 7/2009 |
| WO | 2007105099 | A2 | 9/2007 |
| WO | 2012035757 | A1 | 3/2012 |
| WO | 2012172807 | A1 | 12/2012 |

OTHER PUBLICATIONS

Ozone Solutions, "Ozone Effects on Pathogens," available at https://ozonesolutions.com/blog/ozone-effects-on-pathogens/ (last updated Nov. 10, 2014) (accessed Feb. 24, 2016).

European Patent Office, "Written Opinion of the International Searching Authority," PCT application No. PCT/US2021/012668 (dated May 4, 2021).

International Search Report & Written Opinion, PCT/US2021/012668 (dated Apr. 5, 2021).

* cited by examiner

COVER ASSEMBLY FOR DISINFECTING AN AIR CONDITIONER

RELATED APPLICATIONS

This application claims the benefit under 35 U.S.C. § 119(e) of U.S. Provisional Patent Application No. 62/962,513, titled COVER ASSEMBLY FOR DISINFECTING AN AIR CONDITIONER, and filed on Jan. 17, 2020, the contents of which are incorporated herein by reference in its entirety.

TECHNICAL FIELD

The present disclosure relates generally to cleaning systems for air systems. More specifically, the present disclosure relates to a cover assembly for disinfecting a through-wall air conditioner unit.

BACKGROUND

Air conditioners use compression and expansion of a refrigerant to provide cooled air to a given space. A refrigerant is compressed to a high pressure and then is allowed to expand adiabatically in the air conditioning system. This expansion requires energy and therefore draws energy from the system, resulting in a cooling effect on the unit's cooling coils. A fan blows ambient air over cold coils to transfer heat from the ambient air to the coils. In the process, the ambient air is cooled and then passed into a room or cabin of a vehicle, for example. As the air is cooled by the coils, moisture in the air may also condense on the coils and be collected or allowed to drain from the air conditioning unit.

The figures depict various embodiments of the present disclosure for purposes of illustration only. Numerous variations, configurations, and other embodiments will be apparent from the following detailed discussion.

DETAILED DESCRIPTION

Disclosed is a cover assembly for disinfecting an air conditioning unit and a method of disinfecting an air conditioning unit. In one example, a pliable cover of ozone-resistant fabric is shaped and configured to be releasably installed over the interior portion of a through-wall air conditioning (AC) unit, such as a window-mounted, wall-mounted air conditioning unit, a mini-split unit, or other unit in a building, a recreational vehicle (RV), a camper, a trailer, a tent, or some other interior space. The cover can include magnets, an elastic band, a strap, or other device that is useful to substantially seal the cover to the housing of the AC unit. The cover assembly includes a controller and an ozone generator with pump that can be operated to deliver ozone into the AC unit. In one example, a tube passes through the cover and into the louvers of the AC unit to deliver ozone from the ozone generator to the inside space of the AC unit. Once inside the AC unit, ozone can neutralize mold, bacteria, and odors, and generally disinfect the unit.

The cover optionally defines a vent opening that includes a filter with activated carbon or a catalyst to convert ozone to oxygen. For example, the vent opening is positioned on the front panel of the cover and reduces leaks of ozone into the room by providing a lower-resistance path for ozone escaping from the AC unit. Ozone passing through the filter to the room is converted to oxygen to prevent or reduce ozone being released into the room.

The controller is configured to control general operation of the ozone generator, such as turning on or off the cover assembly and other functions. In one example, the controller is programmable, and the user may use a touch screen, buttons, or other user interface to set the length of operating time, desired concentration of ozone, start time, and other parameters in a program. The controller may additionally receive input from one or more sensors inside and/or outside of the cover that detect ozone concentration, temperature, humidity, and/or other conditions. In some embodiments, the controller adapts the operation of the ozone generator in response to sensor input to achieve the desired ozone concentrations inside the AC unit. In some embodiments, the control panel is integral to the ozone generator. In other embodiments, the control panel is retained by or attached to the cover for easy access by the user, for example.

The controller can cease operation of the ozone generator if a dangerous situation is detected, such as an unacceptable ozone concentration inside the AC unit or ozone leaking into the room. Further, the cover assembly may include a shut-off switch that ceases operation of the ozone generator if the cover is removed from the air conditioning unit. In one example, the shut-off switch results in an open circuit or communication of a signal to the controller when the cover is removed or partially removed from the AC unit. Shut-off similarly can be triggered by a change in capacitance, a detected ozone leak, or other condition.

Overview

The present disclosure provides a disinfecting cover assembly for air conditioning units, including window-mounted air conditioners, through-the-wall air conditioners, and the wall-mounted evaporator unit of "mini-split" air conditioning systems. Such air conditioning systems are commonly used in houses, businesses, recreational vehicles, campers, tents, portable and temporary buildings, trailers, and other enclosed spaces. Such air conditioning systems are rarely cleaned or properly maintained.

During the course of operation, air conditioners often retain standing water and are susceptible to air pollutants. The outside portion of the unit may be subjected to rain, leaves, dirt, and other debris. It is also common for the cooling coils of such units to condense water from the air during the cooling cycle. The condensed water is intended to be drained to the outside, but poor installation or other condition may result in the water being retained in the AC unit. With the presence of water, it is not uncommon for mold and other contaminants to grow inside the unit.

During the offseason, for example, removable air conditioners are commonly stored in basements, garages, or sheds with little or no attention to cleaning or removing the water from the unit prior to storage. To further exacerbate the problem, the storage area may itself be damp, fostering mold growth. During use, the unit may contain water for months or longer as a result of condensation and rain. Similar to window-mounted or through-the-wall air conditioners, the evaporator unit of a mini-split system may accumulate water. Since the evaporator unit is seldom if ever removed from the wall after being installed, moisture inside the evaporator unit can foster growth of mold, bacteria, and the like.

Whether during the off season or during use, a moisture-rich environment in the AC unit is a perfect breeding ground for mold, bacteria, and other germs that can negatively affect the quality of the air coming out of an air conditioner. Compromised air can cause harmful effects (e.g., air conditioner lung) to those who breathe it in, especially those who suffer from allergies and other respiratory conditions. A telltale sign that the air has been compromised is the presence of an unpleasant odor (e.g., a "musty" smell) coming from the air conditioner during operation.

To address the problem of built-up contaminants in air conditioners, some users attempt to clean the unit by wiping down the outside of the AC unit's housing or spraying a cleaner onto the unit's components. However, without disassembling the AC unit, the housing makes it very difficult or impossible to access and clean inside areas of the air conditioner where contaminants reside. Also, when the AC unit is located in a window or installed through a wall opening, the unit may be difficult to access for cleaning, even if the inside of the unit can be accessed. Similarly, the evaporator unit of mini-split systems is often mounted high on an interior wall, making cleaning and maintenance of the evaporator unit difficult at best. Whether from condensation during use or from water entering the AC unit from another source, water inside the AC unit provides a moisture-rich environment that promotes mold growth. Accordingly, a need exists for a system and methodologies to effectively disinfect an air conditioner.

To address this problem and others, the present disclosure relates to a cover assembly that can be installed temporarily over the inside portion of a window-mounted or through-the-wall air conditioner, or on the evaporator unit of a mini-split system, or the like. For example, ozone can be pumped into the air intake of the unit for a time sufficient to disinfect the unit. After doing so, the cover can be removed and the air conditioner's ordinary operation resumed. Numerous variations and embodiments will be apparent in light of the present disclosure.

Example Assemblies

Figure 1A:
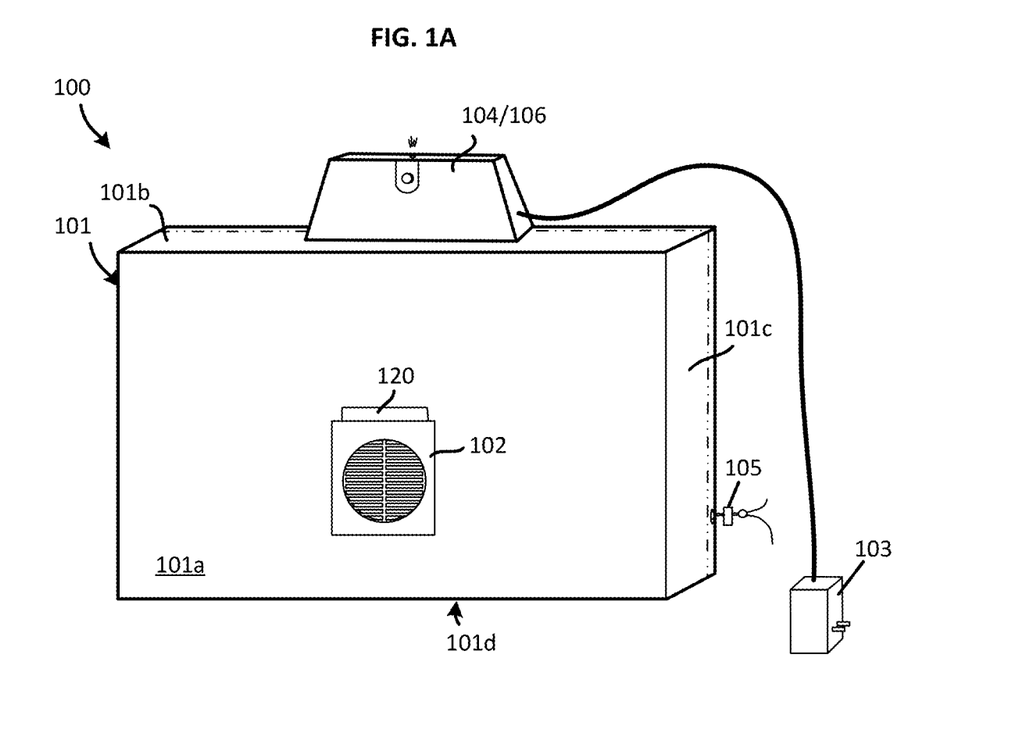
FIGS. 1A-1B illustrate front perspective views of a cover assembly for disinfecting an air conditioning unit, in accordance with some embodiments of the present disclosure.
Figure 1B:
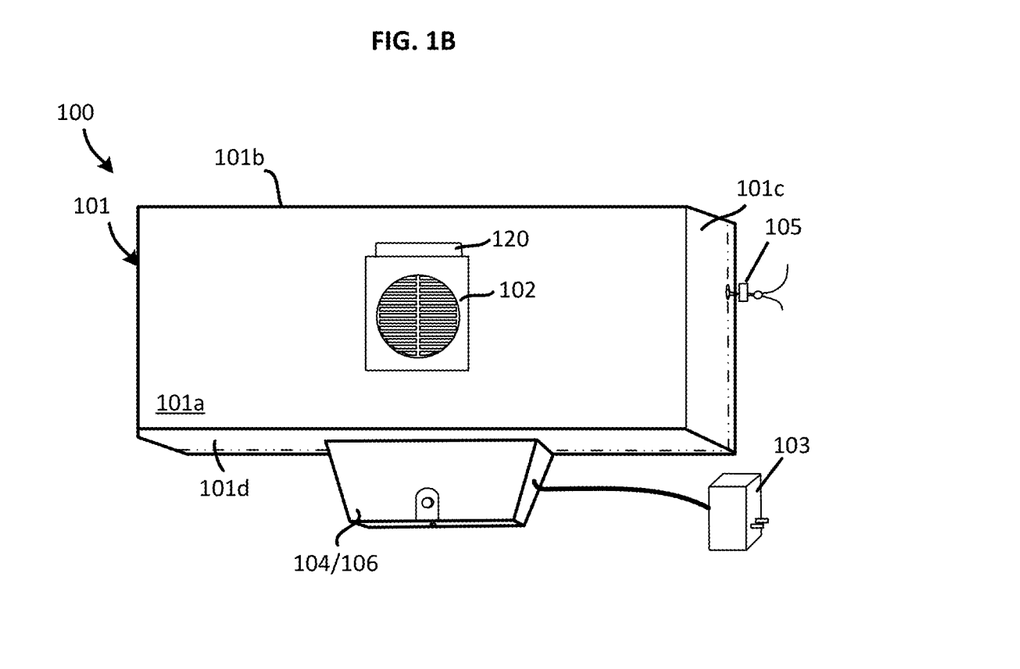

FIGS. 1A and 1B illustrate front perspective views of a cover assembly 100 that can be temporarily installed on an air conditioning (AC) unit and operated to disinfect the unit, in accordance with some embodiments of the present disclosure. In FIG. 1A, the cover assembly 100 is sized and shaped for installation over the inside face of a window-mounted air conditioning unit. In FIG. 1B, the cover assembly 100 is configured to be installed on the evaporator unit of a mini-split system. FIGS. 1A-1B are discussed concurrently below.

The cover assembly 100 includes a cover 101 made of a pliable material and including a front panel 101a, top panel 101b side panels 101c, and bottom panel 101d. The cover 101 generally defines a box-like or cuboid volume that can be fit over the interior portion of an AC unit. In some embodiments, the cover material is impervious or substantially impervious to ozone. In most cases the cover material is made of an ozone-resistant material, such as a urethane laminate, but other materials can be used as deemed suitable for a given application. In one example, the cover 101 is made of a polyester fabric that includes a polyurethane coating. For example, the fabric is a 200-2000 denier fabric, including 200 denier and 600 denier polyester. Such a material can be made waterproof and air-tight through a seam sealing process. In some embodiments, the cover 101 optionally includes a rigid panel to facilitate attachment of the controller 104 and/or ozone generator 106. For example, the top panel 101a of the cover 101 includes a rigid panel coupled to a portion of the pliable material.

The cover 101 includes a closure 105 so that the cover 101 can be snugly fit to the housing of the AC unit. Examples of closures 105 include a drawstring, a cord, an elastic band, a strap, magnets, snaps, or other device. The closure 105 is useful to snugly attach the cover assembly 100 to the AC unit as well as to prevent or reduce leakage from between the cover assembly and the AC housing while the cover assembly 100 is in use. In this example, the closure 105 includes a cord and a cord lock. After installing the cover assembly 100, the cord can be drawn tight around the housing of the AC unit and held with a cord lock, knot, cleat, or other suitable device. The closure 105 can also be an elastic band, an adjustable strap, a plurality of magnets, fasteners, or other structure that maintains the cover 101 in close contact with the AC unit.

Figure 2:
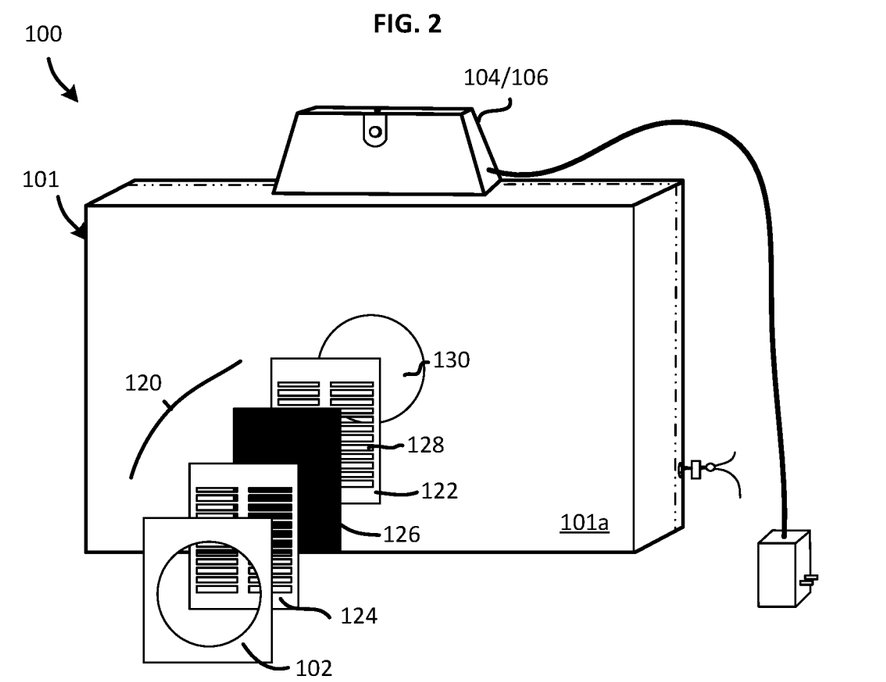
FIG. 2 illustrates a front perspective view of a cover assembly and shows a filter assembly in an exploded view, in accordance with an embodiment of the present disclosure.

In some embodiments, the front panel 101a includes a holder 102 sized to retain a catalyst assembly 120 over a vent opening 130 in the cover 101 (shown in FIG. 2). The vent opening 130 functions to vent air and ozone from inside of the cover 101 and provides a path of reduced resistance so that ozone within the cover 101 preferentially travels through the catalyst assembly 120 rather than leaking through other openings that may exist at corners of the AC unit. The holder 102 can be a pocket, a frame, opposed rails, a bracket, part of a fastener, or the like, where the holder 102 is configured to removably retain the catalyst assembly 120. For example, the installed catalyst assembly 120 is retained over the vent opening 130 and tightly against the front panel 101 by a snug fit in a pocket or by sliding the catalyst assembly 120 into a frame attached to the front panel 101. Side panels 101b optionally can include one or more holders 105, whether over a vent opening 130 or simply to retain spare components of the cover assembly 100.

In other embodiments, the cover 101 is made of a material that includes activated carbon or other catalyst to break down ozone to oxygen. In one example, the cover 101 is lined with a catalyst-laden material or made at least in part with a material that promotes the conversion of ozone to oxygen.

The cover assembly 100 also includes a controller 104 electrically coupled to an ozone generator 106 that includes an air pump, where the controller 104 is configured to control at least basic operation of the ozone generator 106. In these examples, the controller 104 and ozone generator 106 are part of a single component. In some embodiments, a power supply 103 can be used to provide power to the controller 104 and ozone generator 106. In other embodiments, the controller 104 and/or ozone generator 106 can be operated using a battery, a solar cell, or other source of power.

In one example embodiment, the controller 104 includes start/stop functions for the ozone generator 106. In other embodiments, the controller 104 may additionally include one or more additional functions such as a timer, a programmable memory, a sensor input, a shut-off switch, a touch screen or other user interface, lights, sounds, and other features, for example. In one embodiment, the controller 104 is integral to the cover 101, such as being fit into an opening in the top panel 101b or being permanently attached to the top panel 101b. The controller 104 alternately can be attached to the cover 101 in some other location, such as a side panel 101c, front panel 101a, or bottom panel 101d. Note that the controller 104 and ozone generator 106 is mounted to the top panel 101b of the embodiment of FIG. 1A and to the bottom panel 101d of the embodiment of FIG. 1B. The controller/ozone generator 104/106 can be positioned as deemed appropriate for a particular shape or style of air conditioning unit, as will be appreciated.

In some such embodiments, the controller 104 may include one or more sensors that can communicate with an inside of the cover 101 through openings in the cover 101. In other embodiments, the controller 104 is surface mounted and can be releasably attached to the cover 101 using fasteners, hook-and-loop fasteners, clips, magnets, or other suitable means. In other embodiments, the controller 104 is separate from the cover 101 and can be positioned on the top panel 101b, mounted to the nearby wall, or placed in some other location after fitting the cover 101 onto the AC unit. Numerous variations and embodiments will be apparent in light of the present disclosure.

The ozone generator 106 operates based on corona discharge and uses air to generate ozone (O3). The ozone generator 106 includes a pump to deliver generated ozone. The ozone generator 106 can be integral to the controller 104 or can be a separate component that supplies ozone to the cover 101 using a tube 107. In one example, the controller 104 and ozone generator 106 are housed in a single unit attached to or set on the top panel 101b of the cover 101, where the output of the ozone generator 106 is positioned on the inside of the cover 101. In one such embodiment, a tube 107 passes into the cover 101 and can be directed into the louvers of the AC unit. Similarly, when the ozone generator 106 is a separate component, a tube 107 can deliver ozone into the cover 101 and into the AC unit by passing into the cover 101 through an opening, such as a grommet. In some embodiments, the tube 107 is made of an ozone-compatible material, such as ethylene-propylene, fluorosilicone, silicone, stainless steel, fluoropolymer elastomers sold by The Chemours Company as Viton®, or flexible polyethylene tubing that is free of plasticizers and sold by Eldon James as Flexelene®.

Referring now to FIG. 2, a front perspective view shows an exploded view of a catalyst assembly 120 that can be used with the cover assembly 100, in accordance with one embodiment. In this example, the catalyst assembly 120 includes a first support panel 122, a second support panel 124, and a catalyst 126 between the first and second support panels 122, 124. The first and second support panels 122, 124 define one or more openings 128 for gases to flow through, such as air and ozone. The first and second support panels 122, 124 provide structural support to the catalyst 126, which may be a flexible sheet or granules. Depending on the form of the catalyst 126, one or both of the first and or second support panels 122, 124 may be omitted, as will be appreciated.

The catalyst 126 is configured to convert ozone to oxygen and can have any suitable form. The term "catalyst" as used herein includes the catalyst itself as well as a substrate or support medium on which the catalyst may be deposited. The catalyst 126 can be or include activated carbon, magnesium oxide ($Mg_2O_3$) copper oxide (CuO), palladium, platinum, or gold in the form of granules, a coating, a filter containing the catalyst, or reticulated foam that contains or is coated with the catalyst, to name a few examples.

In one example, the catalyst assembly 120 includes an activated carbon filter that can be used by itself or placed between plastic or metal grids. In another example, the catalyst assembly 120 includes granular activated carbon in a disk-like container that can be fit into the vent opening 130. In yet another example, the catalyst assembly 120 is a sheet of reticulated foam coated with or containing activated carbon or other suitable catalyst.

During use of the cover assembly 100, the catalyst assembly 120 is positioned over a vent opening 130 in the front panel 101a and retained by the holder 102. As shown in this example, the catalyst assembly 120 includes an activated carbon filter retained between first and second support panels 122, 124 in a relatively planar form. The catalyst assembly 120 can be installed in the holder 102, which is a pouch or pocket located over the vent opening 130. The cover 101 can have one or more vent openings 130. The vent opening(s) 130 provide a path of reduced resistance for ozone to escape from the cover 101 compared to pathways between the edge of the cover and the exterior of the AC unit, for example. When the catalyst assembly 120 is installed, escaping ozone passes through the catalyst assembly 120 to convert ozone to oxygen, preventing ozone from passing into the room or space where the AC unit is located.

Figure 3:
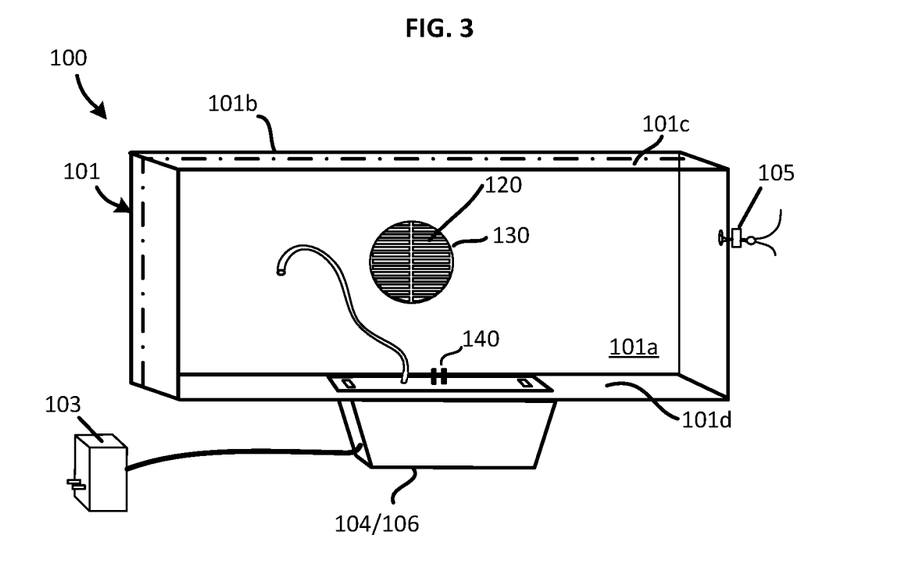
FIGS. 3 and 4 illustrate rear perspective views of a cover assembly for disinfecting an air conditioning unit, in accordance with some embodiments of the present disclosure.
Figure 4:
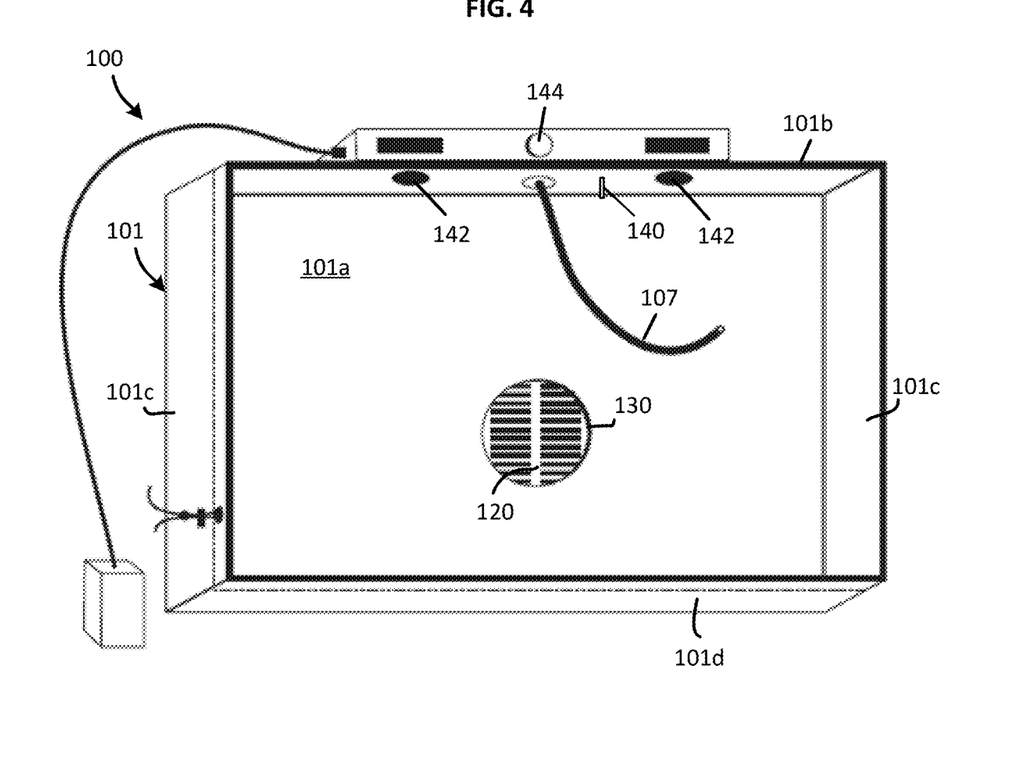

FIGS. 3 and 4 illustrate rear perspective view of a cover assembly 100, in accordance with some embodiments of the present disclosure. In these examples, the controller 104 and ozone generator 106 are combined in a single, integrated unit that is secured to the cover 101, such as on the bottom panel 101d for mini-split units or on the top panel 101b for window-mounted units. In one embodiment, the controller 104/ozone generator 106 can be secured to the cover 101 using fasteners 142. In one embodiment, the fasteners 142 include magnets that are useful to maintain the controller 104 on the air conditioning unit, which typically has a metal housing. A tube 107 connected to the ozone generator 106 delivers ozone to the inside of the cover 101. When the cover 101 is fit onto the AC unit, the tube 107 can be inserted into the air intake or cold-air outlet on the front of the AC unit to deliver ozone into the unit. As also shown in FIGS. 3 and 4, the catalyst assembly 120 can be seen through the vent opening 130 in the front panel 101a.

The cover assembly 100 optionally includes one or more sensors 140 configured and positioned to detect the concentration of ozone inside and/or outside the cover 101. Each sensor 140 uses a wired or wireless connection to communicate a sensed condition to the controller 104. The sensed condition may include any one or more of ozone concentration, humidity, temperature, or other condition. In one example, each sensor 140 is part of the controller 104, where at least one sensor 140 is positioned over or through an opening in the cover 101 to detect the ozone concentration inside of the cover 101. In some such embodiments, the controller 104 includes two or more sensors 140 that communicate with the inside of the cover 101 via an opening or mesh.

During use, the controller 104 may use the sensed condition (e.g., ozone concentration) received from the sensor(s) 140 to terminate operation of the ozone generator 106, such as when ozone concentration exceeds a predetermined maximum value, or when the product of ozone concentration and time meet or exceed a predetermined value. In one embodiment, the controller 104 adjusts operation of the ozone generator 106 to provide the desired ozone concentration and dwell time needed to effectively disinfect the AC unit. For example, the cover assembly 100 is effective to kill at least 99% of viruses and bacteria (and/or inactivate mold and fungi), including at least 99.9%, at least 99.99%, or at least 99.999% of viruses, bacterial, mold, and/or fungi. These levels of disinfection are sometimes referred to as "3-log," "4-log," and "5-log" reduction (or kill rate) in pathogens, respectively.

For example, the ozone generator 106 provides 100-300 ppm ozone inside the AC unit for a period of 5-15 minutes, followed by a dwell time of about 10-20 minutes. In other embodiments, the ozone concentration inside the AC unit is at least 10 ppm, including at least 20, at least 50, at least 100, at least 150, at least 200, and at least 300 ppm. The controller 104 optionally includes one or more sensor 140 on a front face or other portion of the controller 104 to detect ozone concentration or other condition outside of the cover 101. In one embodiment, the maximum value for ozone detected outside of the cover 101 is 2 ppm, 1 ppm, 0.5 ppm, or 0.05 ppm. For example, maximum value for ozone detected outside of the cover 110 is compliant with the US Food and Drug Administration requirements under 21 CFR 801.415.

As shown in FIG. 4, for example, the controller 104 optionally includes a shut-off switch 144 that discontinues operation of the ozone generator 106. In one example, the shut-off switch 144 is a push-button switch on the back of the controller 104. When the cover 101 is properly assembled on the AC unit, the shut-off switch 144 is depressed by contact with the wall, window, window frame, or other structure adjacent the AC unit. In another embodiment, the shut-off switch 144 is between the cover and the air conditioning unit so that when the cover 101 is installed on the unit (e.g., tightened around the unit) the switch is depressed.

In one example, the shut-off switch 144 completes a circuit when depressed and results in an open circuit when not depressed, thereby ceasing operation of the ozone generator 106. Due to the shut-off switch 144 being spring biased to the undepressed position, if the cover 101 is removed or partially removed, the shut-off switch 144 resumes the undepressed state and cuts off power to the ozone generator 106.

In other embodiments, the shut-off switch 140 uses magnetism, a motion detector, a change in capacitance, a proximity sensor, or a sensed condition that, in combination with the controller 104, ceases operation of the ozone generator 106. In some embodiments, the controller 104 sounds an alarm or displays a warning when the shut-off switch 144 is actuated to warn the user that the cover 101 has been disturbed and ozone is present in the area.

Figure 5:
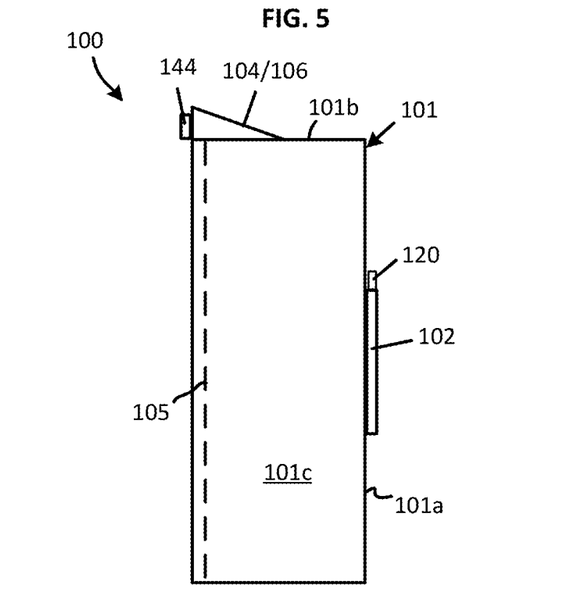
FIG. 5 illustrates a side view of a cover assembly that includes a shut-off switch coupled to the controller, in accordance with an embodiment of the present disclosure.

FIG. 5 illustrates a side view of the cover assembly 100, in accordance with an embodiment of the present disclosure. The shut-off switch 140 protrudes from the back of the controller 104 so as to extend beyond the rear edge of the cover 101. When the cover 101 is properly installed on the AC unit, the shut-off switch 140 is pushed into the controller 104 to complete a circuit and enable operation of the ozone generator 106.

The catalyst assembly 120 is largely contained within the holder 102 on the front panel 101a of the cover 101. In this example, the holder 102 is a pocket or pouch on the front panel 101a and the catalyst assembly 120 is a filter that can be inserted into the pocket.

Figure 6:
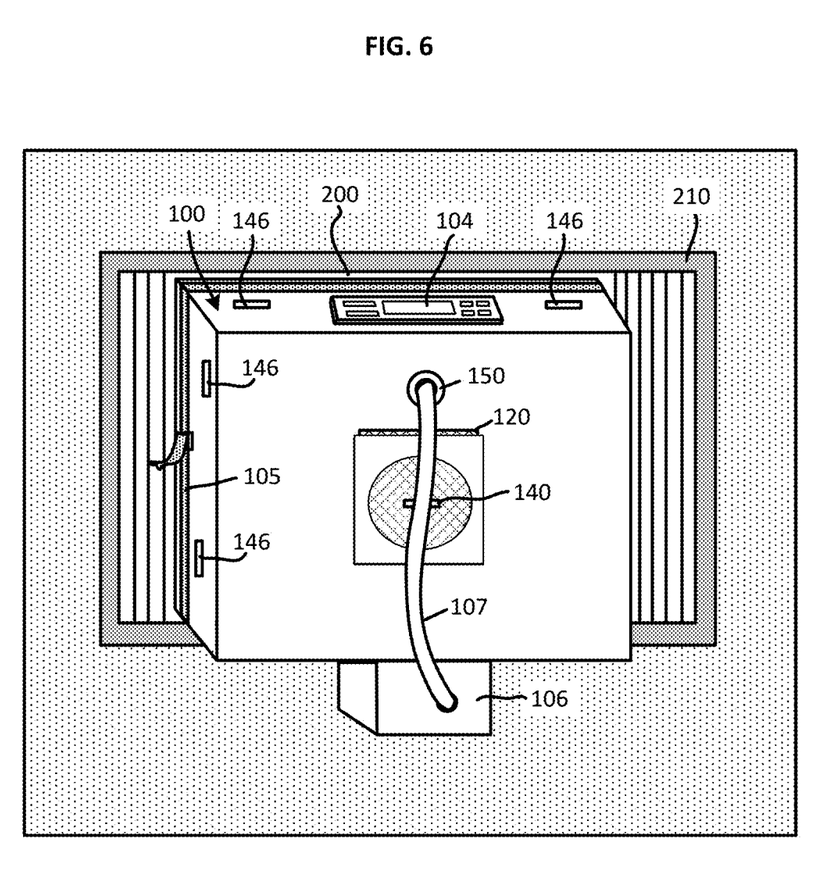
FIG. 6 illustrates a front perspective view of a cover assembly installed on a window air conditioning unit, in accordance with an embodiment of the present disclosure.

FIG. 6 illustrates a front perspective view of a cover assembly 100 installed on the inside portion of an air conditioning unit 200 installed in a wall opening 210. In this example, the ozone generator 106 is separate from the controller 104. The ozone generator 106 is attached to the bottom panel 101d of the cover 101. Ozone is supplied into the cover 101 and to the AC unit 200 using a tube 107 that extends through a grommet 150 in the front panel 101a. After passing through the grommet 150, the tube 107 extends into the louvers of the AC unit 200. In this example, the closure 105 is a strap that can be tightened to secure and substantially seal the cover 101 to the AC unit 200. The cover 101 also includes magnets 146 to retain the cover 101 in contact with the metal housing of the AC unit 200. A sensor 140 on the outside of the cover 101 communicates sensed conditions to the controller 104, such as ozone concentration and temperature of gases exiting the cover 101 through the catalyst assembly 120. After operating the cover assembly 100 to disinfect the AC unit 200, the cover assembly 100 can be removed, and then normal operation of the AC unit 200 resumed.

Figure 7:
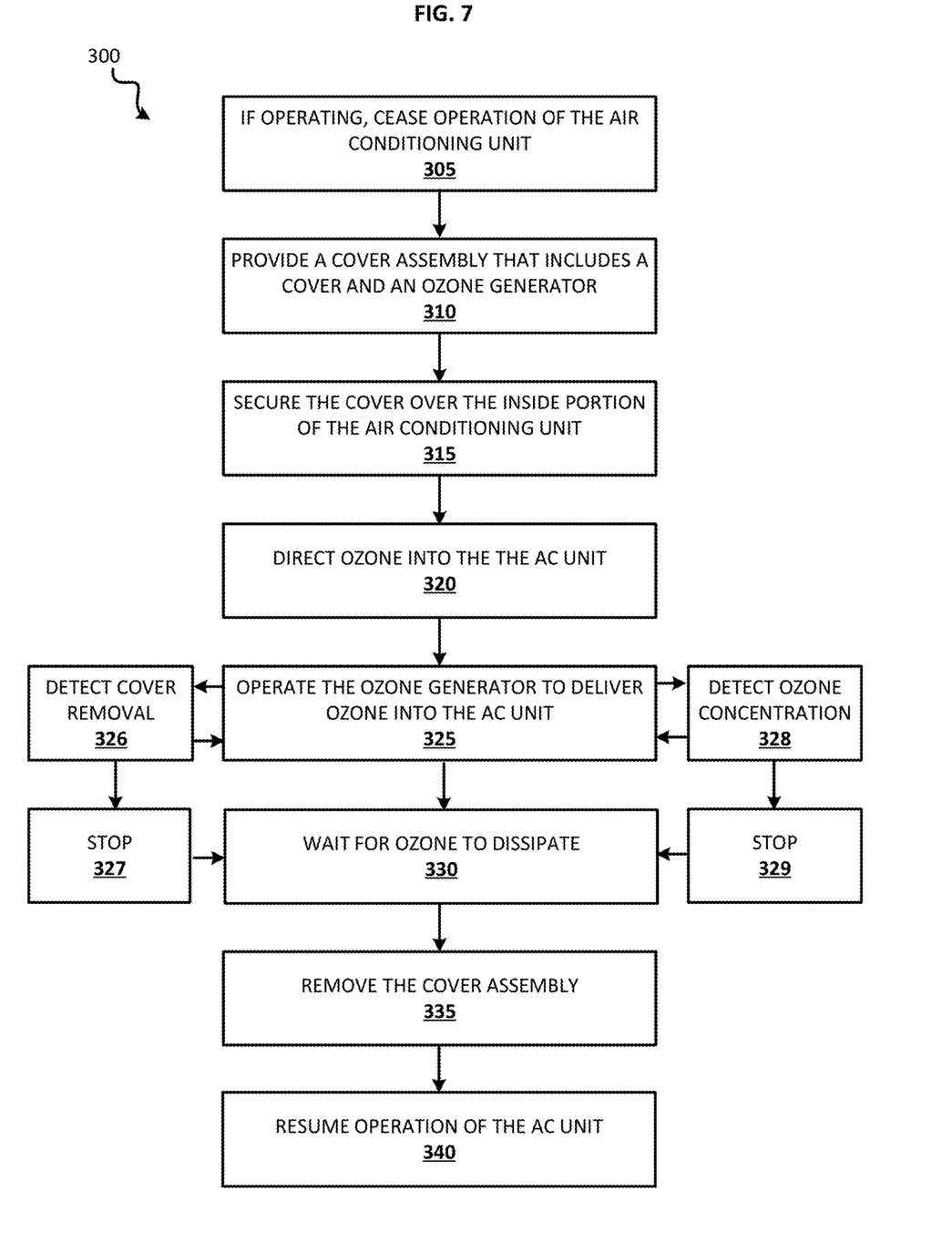
FIG. 7 illustrates a method of disinfecting an air conditioning unit, in accordance with some embodiments of the present disclosure.

FIG. 7 illustrates a method 300 of disinfecting an AC unit 200, in accordance with an embodiment of the present disclosure. Method 300 begins by ceasing operation 305 of an installed AC unit and providing 310 a cover assembly that includes a cover and an ozone generator. Examples of the cover assembly are as discussed above with reference to FIGS. 1-6.

Method 300 continues with securing 315 the cover over the inside part of an air conditioning unit. For example, the cover is placed over the front face and exposed housing of an AC unit that is installed in a window or wall, or an evaporator unit of a mini-split system. The cover is tightened around the housing using a strap or cord. Prior to, during, or after securing 315 the cover on the AC unit, method includes inserting 320 an ozone delivery tube or tubes into the AC unit, such as into louvers on the front of the AC unit. Inserting 320 the tube may include passing the tube through an opening in the cover, then into or towards the louvers of the AC unit. Alternately, the tube or ozone discharge port of the ozone generator can be positioned to direct ozone into the AC unit.

Method 300 continues with operating 325 the ozone generator for a time sufficient to disinfect the AC unit, which may be referred to as a dwell time. In some cases, operating 325 the ozone generator is performed for 1-30 minutes, including 5-25 minutes, 10-20 minutes, 5-15 minutes, or about 7 minutes. Longer operating times may be necessary in some situations, as will be appreciated. During operation, ozone flows into the AC unit to kill or neutralize mold, bacteria, and odors. In one embodiment, the ozone generator provides a concentration of from 1-400 ppm, including at least 10 ppm, at least 50 ppm, at least 100 ppm, at least 150 ppm, at least 200 ppm, at least 250 ppm, at least 300 ppm, 1-150 ppm, 150-350 ppm, 200-400 ppm, 200-300 ppm, 250-350 ppm, or about 300 ppm ozone inside the AC unit.

Optionally, operating 325 the ozone generator includes detecting 326 removal of the cover and/or detecting 328 ozone concentration above a threshold value. If the cover is removed or the ozone concentration exceeds a predetermined limit, for example, the cover assembly (e.g., controller or kill switch) ceases operation of the ozone generator. In some embodiments, operating 325 the ozone generator may include variations in ozone generation to control ozone concentrations inside the cover, and other changes in operation needed to achieve desired ozone concentrations and dwell times.

After operating 325 the ozone generator, method 300 optionally includes waiting 330 for ozone to dissipate or return to a non-toxic state, during which time the cover remains on the AC unit. In one embodiment, waiting 330 is for 10-60 minutes, such as 20-40 minutes, about 30 minutes, or about 10 minutes.

Method 300 continues with removing 335 the cover assembly, at which point normal operation of the AC unit can resume 340 as desired.

Note that the processes in method 300 are shown in a particular order for ease of description. However, one or more of the processes may be performed in a different order or may not be performed at all (and thus be optional), in accordance with some embodiments. Numerous variations on method 300 and the techniques described herein will be apparent in light of this disclosure.

Further Example Embodiments

The following examples pertain to further embodiments, from which numerous permutations and configurations will be apparent Example 1 is a cover assembly for disinfecting an air conditioning unit, the cover assembly comprising a cover made of a pliable material, the cover having a front panel connected to a top panel, a bottom panel, and side panels and generally defining an open-box shape; an ozone generator having an ozone delivery conduit directed into the cover; and a controller operatively coupled to the ozone generator and configured to control operation of the ozone generator.

Example 2 includes the subject matter of Example 1, wherein the cover includes a catalyst for converting ozone to oxygen.

Example 3 includes the subject matter of Example 2, wherein at least a portion the cover is lined with the catalyst.

Example 4 includes the subject matter of any of Examples 1-3, wherein the front panel defines a vent opening and the assembly further comprises a holder configured to retain a catalyst assembly over the vent opening, the catalyst assembly including a catalyst effective to convert ozone to oxygen.

Example 5 includes the subject matter of Example 4 and includes the catalyst assembly comprising a frame with a first frame portion and a second frame portion, the frame sized and shaped to be retained in the holder, and a substrate of a gas-permeable material and including the catalyst on the substrate, wherein the substrate is retained between the first frame portion and the second frame portion.

Example 6 includes the subject matter of any of Examples 1-5 and further comprises a closure on the cover, the closure configured to draw the cover against an outside of the air conditioning unit.

Example 7 includes the subject matter of Example 6, wherein the closure includes one or more of (i) a magnet, (ii) a drawstring, (iii) a cinch, or (iv) an elastic band.

Example 8 includes the subject matter of Example 6, wherein the closure is configured to constrict an opening of the cover defined by the top panel, the side panels, and the bottom panel.

Example 9 includes the subject matter of any of Examples 1-8, wherein the controller is integral to the cover.

Example 10 includes the subject matter of Example 9, wherein the controller is secured to the top panel of the cover.

Example 11 includes the subject matter of any of Examples 1-8, wherein the controller is integral to the ozone generator.

Example 12 includes the subject matter of any of Examples 1-11, wherein the controller includes a graphical user interface.

Example 13 includes the subject matter of any of Examples 1-12 and further comprises one or more sensors in communication with the controller, the one or more sensors configured to detect an ozone concentration.

Example 14 includes the subject matter of Example 13, wherein the one or more sensors are further configured to detect at least one of (i) a temperature, (ii) a capacitance, (iii) a humidity, and (iv) a motion.

Example 15 includes the subject matter of any of Examples 1-14 wherein the ozone delivery conduit includes a tube extending into the cover.

Example 16 includes the subject matter of Example 15, wherein the cover defines an opening sized to receive the tube therethrough.

Example 17 includes the subject matter of any of Examples 1-16 and further comprises a shut-off switch on the cover, the shut-off switch configured to cease operation of the ozone generator when the cover is separated from the air conditioning unit.

Example 18 includes the subject matter of any of Examples 1-17, wherein the cover is made of an ozone-impervious material.

Example 19 is a method of disinfecting an air conditioning unit configured so that when installed, an inside portion of the air conditioning unit is inside an enclosed space with air to be cooled, the method comprising (i) providing a cover assembly that includes a cover sized to be installed on the inside portion of the air conditioning unit, a controller, and an ozone generator, (ii) installing the cover on the inside portion of the air conditioning unit; directing ozone from the ozone generator into the air conditioning unit, and (iii) operating the ozone generator to deliver ozone to an inside of the air conditioning unit.

Example 20 includes the subject matter of Example 19, wherein the air conditioning unit is a window-mounted air conditioner, a through-the wall air conditioner, or an evaporator unit of a mini-split system.

Example 21 includes the subject matter of Example 19 or 20, wherein the enclosed space is selected as a recreational vehicle, a trailer, a camper, or a tent.

Example 22 includes the subject matter of any of Examples 19-21 and further comprises ceasing operation of the air conditioning unit prior to securing the cover on the inside portion of the air conditioning unit.

Example 23 includes the subject matter of any of Examples 19-22, wherein directing the ozone into the air conditioning unit includes directing the ozone into an air intake of the air conditioning unit.

Example 24 includes the subject matter of Example 23, wherein directing the ozone into the air conditioning unit further includes inserting an ozone delivery conduit through an opening in the cover and into the air intake.

Example 25 includes the subject matter of any of Examples 19-24 and further comprises installing a catalyst assembly over a vent opening in the cover, the catalyst assembly including a catalyst effective to convert ozone to oxygen.

Example 26 includes the subject matter of any of Examples 19-25, wherein securing the cover on the inside portion of the air conditioning unit includes depressing a shut-off switch by contact with the air conditioning unit or contact with a surface adjacent the air conditioning unit.

Example 27 includes the subject matter of any of Examples 19-26, wherein the cover assembly includes one or more sensors in communication with the controller, the method further comprising detecting, by the one or more sensors, an ozone concentration; communicating the ozone concentration from the one or more sensors to the controller; and comparing, by the controller, the ozone concentration to a threshold value.

Example 28 includes the subject matter of Example 27, wherein the ozone concentration includes an ozone concentration inside of the cover.

Example 29 includes the subject matter of Example 27 or 28, wherein the ozone concentration includes an ozone concentration outside of the cover.

Example 30 includes the subject matter of any of Examples 27-29 and further comprises ceasing operation of the ozone generator, by the controller, if the ozone concentration exceeds the threshold value.

Example 31 includes the subject matter of any of Examples 27-30 and further comprises the controller communicating a warning of an unsafe condition if the ozone concentration exceeds the threshold value. For example, the warning includes a visible signal, an audible signal, or both.

Example 32 includes the subject matter of any of Examples 27-31 and further comprises detecting, by the one or more sensors, one or more conditions of (i) a temperature, (ii) a capacitance, (iii) a humidity, and (iv) a motion; communicating the one or more conditions from the one or more sensors to the controller; and adjusting, by the controller, operation of the ozone generator based on the one or more conditions.

Example 33 includes the subject matter of Example 32, wherein adjusting the operation of the ozone generator includes changing an ozone output or changing an operating time based at least in part on the temperature.

Example 34 includes the subject matter of Example 32, wherein adjusting the operation of the ozone generator includes changing an ozone output or changing an operating time of the ozone generator based at least in part on the humidity.

Example 35 includes the subject matter of Example 32, wherein adjusting operation of the ozone generator includes ceasing operation of the ozone generator based the one or more conditions.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future-filed applications claiming priority to this application may claim the disclosed subject matter in a different manner and generally may include any set of one or more limitations as variously disclosed or otherwise demonstrated herein.

What is claimed is:

1. A cover assembly for disinfecting an air conditioning unit, the cover assembly comprising:
    a cover made of a pliable material, the cover having a rectangular box shape with a closed end defined by a front panel, and an open end configured to conform to the air conditioning unit when installed thereon, wherein the front panel defines a vent opening;
    an ozone generator having an ozone delivery conduit configured to extend into the cover during use; and
    a controller operatively coupled to the ozone generator and configured to control operation of the ozone generator;
    a holder on the front panel and defining a pocket over the vent opening,
    a catalyst assembly sized to be retained in the holder over the vent opening, the catalyst assembly comprising:
        a frame with a first frame portion and a second frame portion each defining one or more openings, the frame sized and shaped to be retained in the holder in an assembled condition with the first frame portion engaging the second frame portion; and
        a substrate of a gas-permeable configured to be retained between the first frame portion and the second frame portion in the assembled condition including a catalyst on the substrate, wherein when installed in the holder on the front panel, at least part of the one or more openings of the first and second frame portions overlap the vent opening.

2. The cover assembly of claim 1, wherein the cover includes an additional catalyst for converting ozone to oxygen.

3. The cover assembly of claim 2, wherein at least a portion of the cover is lined with the additional catalyst.

4. The cover assembly of claim 1 further comprising a plurality of magnets arranged along the open end of the cover.

5. The cover assembly of claim 1, wherein the open end of the cover has a size that is adjustable by way of a drawstring, a cinch, or an elastic band.

6. The cover assembly of claim 1, wherein the controller is integral to the cover.

7. The cover assembly of claim 6, wherein the controller is secured to a top panel of the cover.

8. The cover assembly of claim 1, wherein the controller is integral to the ozone generator.

9. The cover assembly of claim 1, further comprising one or more sensors in communication with the controller, the one or more sensors configured to detect an ozone concentration and further configured to detect at least one of (i) a temperature, (ii) a capacitance, (iii) a humidity, and (iv) a motion.

10. The cover assembly of claim 1 wherein the ozone delivery conduit includes a tube configured to extend into the inside of the cover through an opening in an upper portion of the front panel, and wherein the tube is configured to extend into the air conditioning unit during use.

11. The cover assembly of claim 1 further comprising a shut-off switch on the cover, the shut-off switch configured to cease operation of the ozone generator when the cover is separated from the air conditioning unit.

12. The cover assembly of claim 1, wherein the cover is made of an ozone-impervious material.

* * * * *